United States Patent [19]

Murray et al.

[11] Patent Number: 4,897,259
[45] Date of Patent: Jan. 30, 1990

[54] HIGH OIL PHASE PHARMACEUTICAL VEHICLES AND SUNSCREEN COMPOSITIONS HAVING WATERPROOF SUN PROTECTION FACTORS

[75] Inventors: Terrence J. Murray, Buffalo; Bhiku G. Patel, Tonawanda; Richard O. Muhlhauser, Grand Island, all of N.Y.

[73] Assignee: Bristol-Myers Company, New York, N.Y.

[21] Appl. No.: 268,105

[22] Filed: Nov. 7, 1988

Related U.S. Application Data

[62] Division of Ser. No. 938,708, Dec. 4, 1986, Pat. No. 4,810,489.

[51] Int. Cl.$^4$ .......................... A61K 7/42; A61K 7/44; A61K 9/10; B01J 13/00
[52] U.S. Cl. .................................... 514/938; 252/309; 252/312; 424/60; 514/847; 514/873
[58] Field of Search ........................... 424/59; 514/938; 252/309, 312

[56] References Cited

U.S. PATENT DOCUMENTS

| | | |
|---|---|---|
| 3,406,238 | 10/1968 | Freyermuth et al. |
| 3,529,055 | 9/1970 | Skoultchi et al. ............ 424/47 |
| 3,670,074 | 6/1972 | Donner ........................ 424/59 |
| 3,728,319 | 4/1973 | Kiesel et al. ................ 424/80 |
| 3,743,715 | 7/1973 | Viout et al. .................. 424/80 |
| 3,784,488 | 1/1974 | Steinhauer et al. ........... 424/59 |
| 3,821,363 | 6/1974 | Black et al. .................. 424/59 |
| 3,864,473 | 2/1975 | Ciaudelli ..................... 424/60 |
| 3,895,104 | 7/1975 | Karg ........................... 424/59 |
| 4,128,633 | 12/1978 | Lorenz et al. ................ 424/80 |
| 4,172,122 | 10/1979 | Kubik et al. .................. 424/59 |
| 4,241,048 | 12/1980 | Durbak et al. ................ 424/45 |
| 4,426,374 | 1/1984 | Wheeler ....................... 424/60 |
| 4,567,038 | 1/1986 | Ciaudelli et al. ............. 424/59 |
| 4,597,963 | 7/1986 | Deckner ....................... 424/59 |

FOREIGN PATENT DOCUMENTS

| | | | |
|---|---|---|---|
| 1196868 | 12/1981 | Canada ........................ | 424/78 |
| 1196577 | 1/1983 | Canada ........................ | 424/59 |
| 193387 | 2/1986 | European Pat. Off. ........... | 424/59 |

OTHER PUBLICATIONS

Kaidbey et al., Journal of the American Academy of Dermatology, vol. 4, No. 5, pp. 566-570, (May 1981).
Sun Care Market, Household and Personal Products Industry (HAPPI), Rodman Publishing Corp., Ramsey, N.J., pp. 32-38 (Sep. 1986).
Berger et al., J. Soc. Cosmet. Chem., vol. 29, pp. 641-649 (1978).
Sun Products Documentary/Formulary/Encyclopedia, Cosmetics & Toiletries, vol. 98, pp. 99-106 (Mar. 1983).
Leroy et al., Photodermatology, vol. 3, No. 1, pp. 52-53 (Feb. 1986).
Fogel, Cosmetics & Toiletries, vol. 98, pp. 91-98 (Mar. 1983).
Amphisol Suntan Emulsions, Bernel Chemical Co., Inc., P.O. Box 777, Tenafly, N.J. 07670.
Pathac, J. Am. Acad. Dermatol, vol. 7, No. 3, pp. 285-312 (Sep. 1982).
Sayre et al., J. Soc. Cosmet. Chem., Col. 31, pp. 133-143 (May/Jun. 1980).
Roelandts et al., Int. J. Dermatol., vol. 22, pp. 247-255 (1983).

Primary Examiner—Dale R. Ore
Attorney, Agent, or Firm—David M. Morse

[57] ABSTRACT

High oil phase pharmaceutical vehicles in the form of an emulsion system having an oil phase content of from about 35% to about 65%, wherein the emulsion system comprises from about 1% to about 13% of an alkylated PVP copolymer, from about 1% to about 7% of an emulsifier, and a solvent system. The solvent system comprises from about 4% to about 18% of a $C_4$-$C_{22}$ fatty acid, alcohol or ester thereof, from about 2% to about 25% of a glycol ester or diester, and from 0% to about 13% of a branched chain ester of a $C_4$-$C_{22}$ carboxylic acid. The pharmaceutical vehicles are useful in sunscreen formulations, and especially those containing higher concentrations of benzophenone-3. When such higher concentrations are used, it is advantageous to add up to about 10% of a branched chain ester of a $C_4$-$C_{22}$ carboxylic acid.

9 Claims, No Drawings

HIGH OIL PHASE PHARMACEUTICAL VEHICLES AND SUNSCREEN COMPOSITIONS HAVING WATERPROOF SUN PROTECTION FACTORS

This is a division of our prior co-pending application Ser. No. 938,708 filed December 4, 1986, now U.S. Pat. No. 4,810,489.

FIELD OF THE INVENTION

This invention relates to high oil phase pharmaceutical vehicles and waterproof sunscreen compositions containing those pharmaceutical vehicles.

BACKGROUND OF THE INVENTION

Sunscreen formulations for use on human skin are well known, and many different types are commercially available to satisfy diverse consumer needs. For example, sunscreen formulations having different sun protection factor (SPF) values are available, thus allowing consumers to choose the amount of protection desired. SPF values range from zero upward with higher values indicating greater amounts of sun protection. SPF values of 2-4 indicate minimal sun protection, 4-6 indicate moderate sun protection, 8-15 indicate maximal sun protection, and above 15 indicate ultra sun protection.

One important consideration when choosing a sunscreen is whether it resists coming off in water. "Water resistant" formulations can undergo about 40 minutes in water without significant SPF loss, whereas "waterproof" formulations can undergo about 80 minutes in water without significant SPF loss. Waterproof formulations can be especially desirable because they eliminate the need for reapplication after swimming, bathing or excessive perspiration.

Other considerations can also be important when choosing a sunscreen product. For example, certain individuals are allergic to sunscreen compositions that contain p-aminobenzoic acid (PABA) or derivatives thereof, which are especially prevalent in higher SPF formulations. Furthermore, PABA and derivatives thereof cause stains which may be especially problematic and irritating to boat owners.

Thus, it obviously would be desirable to formulate waterproof sunscreen compositions, some of which do not contain PABA.

Certain UV A sunscreen agents such as 2-hydroxy-4-methoxybenzophenone, commonly referred to as benzophenone-3 or oxybenzone, are often used in conjunction with UV B type sunscreen agents to effect a broader spectrum of sunscreen protection. Benzophenone-3 absorbs ultraviolet rays in the higher UV A range of about 3200-4000 Angstrom wavelengths, whereas UV B sunscreen agents such as PABA absorb ultraviolet rays in the more harmful and burning 2800-3200 Angstrom wavelength range. Benzophenone-3 is often difficult to solublize and keep in solution, especially in the presence of water. It is more soluble in PABA esters such as octyl dimethyl PABA then it is in water or alcohol. Higher concentrations of benzophenone-3 (up to about 6% by weight) are desirable when formulating sunscreens having higher SPF values. Heretofore, however, it has been difficult to achieve stable concentrations containing benzophenone-3 at concentrations greater than about 3%. In fact, some products having higher concentrations maintain the benzophenone-3 in suspension rather than in solution.

A second problem confronted when formulating waterproof sunscreens is providing acceptable consistency, skin-feel and stability to the product. Those factors, which are important to achieving consistent distribution on the skin, even sun protection, consumer acceptance, and commercial viability, are largely functions of the vehicle which carries the sunscreen agents.

For the above reasons, it would clearly be desirable to formulate a pharmaceutical vehicle capable of providing acceptable consistency, skin-feel and stability, and which is also capable of solubilizing higher concentrations of benzophenone-3 and/or other sunscreen agents.

With that in mind, we investigated the use of copolymers of polyvinylpyrrolidone (PVP) and long alkyl chain olefins, more commonly known as alkylated PVP's. Such copolymers have been produced for over twenty years by GAF Corporation, 1461 Alps Road, Wayne, New Jersey, under the tradename Ganex resins. Ganex resins were chosen because they are known to impart waterproof and moisture barrier properties to various skin care products, including sunscreens. To date, however, no Ganex-containing compositions have been produced that can satisfactorily solubilize benzophenone-3 (especially in higher concentrations) to produce a sunscreen having acceptable consistency, skin-feel and stability.

It has now been discovered, that high oil phase waterproof pharmaceutical vehicles comprising Ganex resins and the unique solvent systems disclosed herein possess an unexpectedly superior ability to solubilize sunscreen agents, including concentrations up to about 6% by weight of benzophenone-3. Furthermore, it has been found that the pharmaceutical vehicles themselves play a significant part in determining SPF values, and in some cases, can contribute to a very high final waterproof SPF values that others cannot achieve.

All of the weight percentages listed herein are weight percentages based upon the total weight of the pharmaceutical vehicle or sunscreen formulation.

SUMMARY OF THE INVENTION

We have discovered a waterproof pharmaceutical vehicle in the form of an emulsion system having an oil phase content of from about 35% to about 65%, wherein the emulsion system comprises from about 1% to about 10% of an oil soluble polyvinylpyrrolidone and long alkyl chain olefin copolymer, from about 2% to about 10% of an emulsifier, and a solvent system comprising from about 4% to about 20% of a $C_4$-$C_{22}$ fatty acid, alcohol or ester thereof, from about 4% to about 25% of a glycol ester or glycol diester, and from 0% to about 13% of a branched chain ester of a $C_4$-$C_{22}$ carboxylic acid.

We have also discovered a waterproof sunscreen formulation in the form of an emulsion system having an oil phase content of from about 35% to about 65%, wherein the emulsion system comprises form about 1% to about 10% of an oil soluble polyvinylpyrrolidone and long alkyl chain olefin copolymer, from about 2% to about 10% of an emulsifier, a solvent system comprising from about 4% to about 20% of a $C_4$-$C_{22}$ fatty acid, alcohol or ester thereof, from about 4% to about 25% of a glycol ester or diester, and from about 0% to about 10% of a branched chain ester of a $C_4$-$C_{22}$ carboxylic acid, and from about 1% to about 25% of at least one sunscreen agent.

DETAILED DESCRIPTION OF THE INVENTION

The waterproof pharmaceutical vehicles of this invention are emulsion systems having an oil phase content of from about 35% to about 65% by weight of the pharmaceutical vehicle. The emulsion system comprises a polyvinylpyrrolidone and long alkyl chain olefin copolymer, an emulsifier, and a solvent system. The sunscreens of this invention basically comprise the pharmaceutical vehicles of this invention in combination with one or more sunscreen agents. Each of the above ingredients is discussed below in greater detail.

Polyvinylpyrrolidone (PVP)/Long Alkyl Chain Olefin Copolymers

Numerous oil soluble alkylated PVP copolymers, including those sold by GAF under the tradename Ganex resins, are known and useful in this invention. It has been found that Ganex V-216, which is a liquid PVP/hexadecene copolymer, and Ganex V-220, which is a solid PVP/eicosene copolymer, can provide satisfactory results. The Ganex V-220 resins have provided the best results, particularly in terms of emulsion stability and higher SPF values.

Generally, from about 1% to about 10% of alkylated PVP copolymer will be present in the pharmaceutical vehicles of this invention. The preferred range is from about 2.5% to about 7.5%. Likewise from about 1% to about 10% of alkylated PVP copolymer will be present in the sunscreen formulation of this invention. The preferred range is from about 2.5% to about 7.5%, with about 5% providing acceptable results.

Solvent System

The solvent system invention basically comprises a combination of two or three particular ingredients, depending on the type and concentration of sunscreen agent to be added to the vehicle.

The first ingredient is a $C_4$–$C_{22}$ fatty acid, alcohol or ester thereof, which can be present in amounts of from about 4% to about 20% in the pharmaceutical vehicle with the preferred range being from about 6% to about 15%. Sunscreen formulations will normally contain from about 4% to about 20%, with from about 8% to about 12% preferred. About 10% has provided acceptable results.

Natural and synthetic $C_4$–$C_{22}$ fatty acids, alcohols and esters thereof are well known in the art. Such compounds can include capric acid, lauric acid, myristic acid, palmitic acid, oleic acid, stearic acid, hydroxystearic acid, arachic acid, ricinoleic acid, linolenic acid, linoleic acid, their corresponding alcohols, and esters. Isopropyl myristate has been found to provide acceptable results.

The second ingredient in the solvent system is a glycol ester or a glycol diester such as a cosmetic ester with emmollient properties which combine the non-occlusive lubricity of a branched chain ester with the non-oily characteristics of a diester. Diesters will reduce the greasy oily feel without adversly affecting rub-in properties. The glycol ester or diester can be present in the pharmaceutical vehicle in amounts of from about 4% to about 25%, with the preferred range being from about 4% to about 20%. Sunscreen formulations will normally contain from about 4% to about 25%, with from about 4% to about 16% being preferred.

Glycol esters and diesters are also well known in the art. Such compounds can include the esters and diesters of propylene glycol, butylene glycol, diethylene glycol, dipropylene glycol, hexylene glycol, polyethylene glycol, polypropylene glycol, and their esters. Propylene glycol dioctanoate has been found to provide acceptable results.

The addition of a third ingredient, a branched chain ester of a $C_4$–$C_{22}$ carboxylic acid, to the solvent system has proven advantageous when higher concentrations of benzophenone-3 are added to sunscreens of this invention. As previously discussed, it has heretofore been very difficult to keep greater than about 3% benzophenone-3 in solution. It has been found that adding from about 3% to about 10% and preferably from about 5% to about 8% of the branched chain ester will help prevent concentrations of up to 6% benzophenone-3 from crystallizing out of solution. (Concentrations of benzophenone-3 greater than 6% are generally not permitted.) Of course, such branched chain esters can be used in the pharmaceutical vehicles of this invention (where no sunscreen agents are present), and also in sunscreens of this invention that do not contain benzophenone-3. When used in the pharmaceutical vehicle, they will normally be present in amounts up to about 13%, with from about 5% to about 11% being preferred. Branched chain esters of $C_4$–$C_{22}$ carboxylic acids are also well known, and include isodecyl neopentanoate, which has provided acceptable results.

Emulsifier

Emulsifiers suitable for use in the present invention can be any of a wide variety disclosed in the prior patents and other references. Two patents, incorporated by reference herein, which disclose suitable emulsifiers are U.S. Pat. No. 3,755,560, August 28, 1973 to Dickert et al. and U.S. Pat. No. 4,421,769, December 20, 1983 to Dixon et al. Preferred emulsifiers are anionic or nonionic although other types may also be used. Another reference disclosing an extensive number of emulsifiers is McCutcheon's *Detergents & Emulsifiers*, North American Edition, 1983, incorporated herein by reference.

Suitable emulsifier types include ethoxylated fatty acids, ethoxylated esters, ethoxylated ethers, ethoxylated alcohols, phosphated esters, polyoxyethylene fatty ester phosphates, fatty acid amides, acyl lactylates, soaps and mixtures thereof. Fatty alcohols such as cetyl and stearyl alcohol and cetearyl alcohol are also regarded as emulsifiers for purposes of the present invention.

Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium stearoyl-2-lactylate and calcium stearoyl-2-lactylate. Soaps are also acceptable emulsifiers. The soaps may be formed in situ in processing the composition and are preferably alkali metal or triethanolamine salts of long chain fatty acids. Such soaps include sodium stearate, triethanolamine stearate and the similar salts of lanolin fatty acids. The emulsifier, or mixture of emulsifiers, is normally present at a level of from about 2% to about 10%, and preferably from about 2% to about 5%.

A one part emulsifier comprising cetyl phosphate and DEA cetyl phosphate has been found to provide acceptable results. Such an emulsifier is manufactured by Givaudan, 100 Dalawanna Ave., Bliston, N.J. under the trade name Amphisol. The normal range of Amphisol in the pharmaceutical vehicle can be from about 1% to about 7%, with from about 2% to about 5% being preferred. Generally, from about 1% to about 5% of the Amphisol can be present in sunscreen formulations of this invention, and preferably from about 2% to about 4%. About 2.5% has been found to provide acceptable results.

Optional Components

The compositions of the present invention may contain in addition to the aforementioned essential components a wide variety of additional oil soluble materials and water soluble materials.

Among the optional oil soluble materials are nonvolatile silicone fluids such as polydimethyl siloxanes with viscosities ranging from about 10 to about 100,000 centistokes at 25° C. These siloxanes are available from Dow Corning Corporation as the Dow Corning 200 series.

Other oil soluble materials include oils such as castor oil, jojoba oil, cottonseed oil, peanut oil and sesame oil; waxes such as petrolatum, ceresin wax, carnauba wax, beeswax, and castor wax; lanolin, its derivatives and components such as acetylated lanolin, lanolin alcohols and lanolin fatty acids.

The oil phase materials can comprise from about 35% to about 65% of the total composition. The balance of the composition is usually water.

The present compositions may also contain agents suitable for aesthetic purposes such as perfumes, dyes, thickening agents and preservative agents to prevent microbial growth.

Sunscreen Agent

The term "sunscreen agent" as used herein includes commonly used ultraviolet ray-blocking compounds such as ethylhexyl p-methoxycinnamate, butyl methoxydibenzoylmethane, 2-hydroxy-4-methoxybenzophenone (benzophenone-3), octyl dimethyl p-aminobenzoic acid, digalloyl trioleate, 2,2-dihydroxy-4-methoxy benzophenone, ethyl 4-[bis(hydroxypropyl)] aminobenzoate, 2-ethylhexyl 2-cyano-3,3-diphenylacrylate (octocrylene), ethyl hexyl p-methoxy cinnamate, 2-ethylhexyl salicylate, glyceryl p-aminobenzoate, 3,3,5-trimethylcyclohexyl salicylate, methyl anthranilate, p-dimethyl aminobenzoate and 2-ethylhexyl p-dimethyl amino benzoate. Mixtures of these compounds may also be used. A more detailed discussion of sunscreen agents useful in this nivention is provided by Roelandts et al., *A Survey of Ultraviolet Absorbers in Commercially Available Sun Products*, INT. J. DERMATOL., Vol. 22, pp. 247–255 (May 1983).

The amount of sunscreen agents useful in the sunscreen compositions of the present invention is from about 1% to about 25%, with the exact percentage dependent upon the particular agent chosen and SPF desired.

Table I, which follows, provides numerous examples of sunscreen formulations prepared in accordance with this invention. These examples merely illustrate this invention and do not in any way limit the scope of this invention.

TABLE I

| Formulation | Octo-cylene | Octyl Di-methyl PABA | Octyl Meth-oxycin-namate | Benzo-phe-none-3 | Octyl Salic-ylate | Ganex 216 | Ganex 220 | Glyc-erin | Sili-cone 200 | Sili-cone 225 | Isodecyl Neo-pentan-oate | Fra-grance | Iso-propyl Myris-tate | P.G. Di-octanoate | SPF Values Obtained After 80 Minutes in a Whirlpool/ Swimming Pool | | |
|---|---|---|---|---|---|---|---|---|---|---|---|---|---|---|---|---|---|
| FN5-796-20 | — | — | 7% | 3% | 3% | x | — | x | x | — | — | — | 4% | 4% | <9.6 | <9.6 | 12 |
| FN5-796-21 | — | — | 7% | 6% | 5% | x | — | x | x | — | — | — | 5% | 4% | 15 | 15 | 15 |
| | | | | | | | | | | | | | | | 12 | 18.75 | <9.6 |
| FN5-796-24 | — | — | — | 6% | 5% | x | — | x | x | — | — | — | 5% | 4% | <9.6 | <9.6 | <9.6 |
| FN5-822-22 | — | — | 7% | 6% | 5% | x | — | x | x | — | — | — | 7% | 4% | <9.6 | <9.6 | 12 |
| FN5-822-23 | — | — | 7% | 6% | 5% | — | x | — | x | — | — | — | 7% | 4% | <9.6 | 12 | 15 |
| FN5-822-24 | — | — | 7% | 6% | 5% | — | x | — | — | — | — | — | 7% | 4% | <9.6 | <9.6 | <9.6 |
| Suncare 15 | — | 8% | — | 3% | — | — | x | — | — | — | — | — | | | 15 | 15 | 15 |
| FN5-849-01 | — | — | 7% | 6% | 5% | x | — | x | — | x | — | — | 10% | 4% | 23 | 15 | 18.75 |
| FN5-849-02 | 10% | — | 7% | 6% | — | — | x | 2% | — | x | — | — | 10% | 4% | 12 | <9.6 | <9.6 |
| | | | | | | | | | | | | | | | 18.75 | 18.75 | |
| FN5-849-08 | — | — | 7% | 6% | 5% | x | — | — | x | — | — | — | 10% | 6% | 12 | 12 | 12 |
| FN5-849-12 | 10% | — | 7% | 6% | — | — | x | — | — | x | — | — | 10% | 4% | >23 | >23 | >23 |
| | | | | | | | | | | | | | | | 15 | 15 | 23 |
| FN5-849-14 | 7% | — | 5% | 3% | — | — | x | — | — | x | — | — | 10% | 4% | 12 | <9.6 | <9.6 |
| FN5-849-20 | 7% | — | 5% | 6% | — | — | x | — | — | x | — | — | 10% | 4% | 18.75 | 15 | 15 |
| FN5-849-22 | — | — | 7% | 6% | — | — | x | — | — | x | — | — | 10% | 4% | 12 | 12 | 12 |
| FN5-849-23 | 10% | — | — | 6% | — | — | x | — | — | x | — | — | 10% | 4% | 23 | 23 | 23 | 23 |
| FN5-849-26 | — | 8% | — | 6% | — | — | x | — | — | x | — | — | 10% | 4% | 18.75 | 15 | 15 |
| FN5-849-34 | — | 8% | — | 6% | — | — | x | — | — | x | — | — | 10% | 10% | 23 | 15 | 18.75 |
| | | | | | | | | | | | | | | | 15 | 12 | 12 |
| FN5-849-36 | — | — | 7% | 6% | — | — | x | — | — | x | — | — | 10% | 10% | 23 | >23 | 23 | * 23 |
| FN5-849-40 | — | 8% | — | 3% | — | — | x | — | — | x | — | — | 10% | 10% | <9.6 | <9.6 | <9.6 |
| FN5-849-48 | — | 8% | 7% | 6% | — | — | x | — | — | x | 5% | x | 10% | 5% | 12 | 18.75 | 18.75 |
| Solbar 15 | 10% | — | 8% | 5% | — | — | x | — | — | x | — | x | | | 23 | <9.6 | <9.6 |
| FN6-872-01 | — | 3% | 7% | 6% | — | — | x | — | — | x | — | x | 10% | 4% | 29 | 29 | >29 |
| FN6-872-02 | — | — | 7% | 6% | 5% | — | x | — | — | x | 5% | — | 10% | 10% | 15 | 15 | 15 | 23 |
| FN6-872-03 | — | — | 7% | 6% | — | — | x | — | — | x | 5% | — | 10% | 15% | 15 | 23 | 23 |
| FN6-872-04 | 10% | — | 7% | 6% | — | — | x | — | — | x | 5% | — | 10% | 4% | 12 | 12 | 12 | 23 |
| FN6-872-05 | — | 5% | — | 3% | — | — | x | — | — | x | — | — | 10% | 13% | <9.6 | 15 | 15 |
| FN6-872-06 | — | 4% | — | 3% | — | — | x | — | — | x | — | x | 10% | 14% | <9.6 | 18.75 | 18.75 |
| | | | | | | | | | | | | | | | <9.6 | 23 | 23 |
| FN6-872-07 | — | 3% | — | 3% | — | — | x | — | — | x | — | x | 10% | 15% | 23 | 23 | 23 |
| | | | | | | | | | | | | | | | 8 | 10 | 10 | >12.5 |
| FN6-872-08 | — | 2% | — | 3% | — | — | x | — | — | x | — | x | 10% | 16% | >12.5 | >12.5 | 12.5 |
| FN6-872-09 | — | 8% | — | 6% | — | — | x | — | — | x | 5% | x | 10% | 10% | 6.25 | >6.25 | >6.25 | 6.4 |
| | | | | | | | | | | | | | | | 6.4 | 10 | 12.5 |
| | | | | | | | | | | | | | | | 6.25 | 6.25 | 6.25 |
| | | | | | | | | | | | | | | | 23.4 | 23.4 | >29 |
| FN6-872-10 | — | 2% | — | 2% | — | — | x | — | — | x | — | x | 10% | 16% | >23 | >23 | 23 | 23 |
| FN6-872-11 | — | 1.5% | — | 2% | — | — | x | — | — | x | — | x | 10% | 16% | >6.25 | >6.25 | >6.25 |
| W 1072-M-15-A | — | 1.5% | 7% | — | — | — | x | — | — | x | — | x | | | 6.25 | 6.25 | 6.25 |
| | | | | | | | | | | | | | | | 5 | 4 | 4 |
| W 1074-M-26-A | 10% | — | — | 6% | — | — | x | — | — | x | — | x | | | 18.75 | >29.3 | >29.3 | 3.2 >29.3 |

TABLE I-continued

| Formulation | Octo-cyrlene | Octyl Di-methyl PABA | Octyl Meth-oxycin-namate | Benzo-phe-none-3 | Octyl Salic-ylate | Ganex 216 | Ganex 220 | Glyc-erin | Sili-cone 200 | Sili-cone 225 | Isodecyl Neo-pentan-oate | Fra-grance | Iso-propyl Myris-tate | P.G. Di-octanoate | SPF Values Obtained After 80 Minutes in a Whirlpool/ Swimming Pool | |
|---|---|---|---|---|---|---|---|---|---|---|---|---|---|---|---|---|
| W 1074-M-27-A | — | — | 7% | 6% | 5% | — | x | — | — | x | 5% | — | 10% | 8% | >29.3 | 29.3 |
| W 1074-M-28-A | — | 5% | — | 6% | — | — | x | — | — | x | 8% | x | 10% | 10% | >29.3 | 18.75 |
| W 1074-M-27-A | — | — | 7% | 6% | 5% | — | x | — | — | x | 5% | — | 10% | 8% | >29.3 | 29.3 |
| W 1074-M-25-A | — | 8% | 7% | 6% | — | — | x | — | — | x | 5% | x | 10% | 5% | >29.3 | 29.3 |
| W 1072-M-16-A | — | 2% | — | — | — | — | x | — | — | x | — | x | 10% | 16% | SPF = 29.1, n = 21 | |
| FN6-872-09 (W 1074-M-23-A) | — | 8% | — | 6% | — | — | x | — | — | x | 5% | x | 10% | 10% | SPF = 29.1, n = 18 | |
| FN6-872-01 (W 1074-M-21-A) | 10% | — | 7% | 6% | — | — | x | — | — | x | — | x | 10% | 4% | SPF = 4.5, n = 24 | |
| FN6-849-23 (W 1074-M-19-A) | 10% | — | 7% | 6% | — | — | x | — | — | x | — | — | 10% | 4% | 27.9 | |
| W 1073-M-15-A | — | 4% | — | 3% | — | — | x | — | — | x | — | x | 10% | 14% | 29.3 | |
| W 1072-M-15-A | — | 1.5% | — | — | — | — | x | — | — | x | — | x | 10% | 16% | 28.8 | |
| W 1074-M-28-A | — | 5% | — | 6% | — | — | x | — | — | x | 8% | x | 10% | 10% | 11.3 | |
|  |  |  |  |  |  |  |  |  |  |  |  |  |  |  | 3.8 | |
|  |  |  |  |  |  |  |  |  |  |  |  |  |  |  | 23.0 | |

*Swimming Pool

From Table I, certain general trends can be noted in the SPF values obtained. For example, in looking at the results comparing formulas FN5-796-20, FN6-849-14, and FN6-849-40 (all with 3% benzophenone-3) with FN5-796-21, FN6-849-20, and FN6-849-34 respectively (all with 6% benzophenone-3), it can be seen that the addition of 6% benzophenone-3 to the respective formulas gave a general increase in the waterproof SPF mean values in all 3 cases.

In the original starting experiments, a non-PABA (non-octyldimethyl PABA-containing) composition was desired so compositions containing 7% OMC, 3% benzophenone-3, and 5% octyl salicylate were prepared. Oil-soluble Ganex V-216 was employed as the polymer and glycerin was included as a humectant. The waterproof SPF numbers obtained, however, were quite low and the potential wash-off characteristics of this combination were not considered to be good. A switch to Ganex V-220, a solid eicosene/PVP copolymer was made from Ganex V-216, a liquid hexadecene/PVP copolymer to facilitate incorporation of 5% of the copolymer and improve emulsion stability. Ganex V-216 on aging tended to thin-out and separate from those formulas which did not contain glycerin and the glycerin-containing formulas had low SPF values. Ganex V-220 gave more stable formulas but Ganex V-216 could probably be used if some necessary changes were made to the formulation.

After the switch to Ganex V-220, results were still low on the SPF waterproof testing as compared to Suncare 15 (an 8% OD PABA-containing formulation manufactured by Elizabeth Arden). A combination of 7% octyl methoxycinnamate (OMC), 6% benzophenone-3, and 5% octyl salicylate with Ganex V-216 and glycerin gave one value of 15 but two other individuals tested as 9.6 (FN5-849-01). FN5-849-02 (with Ganex V-220) was only marginally better, even after addition of 10% octocrylene. Since the glycerin might be contributing to wash-off of the sunscreens, it was decided to drop the glycerin and add 10% octocrylene. Thus FN5-849-12 gave the first really high SPF values, 23 in 5 of 6 patients. Reduction of the octocrylene to 7% and dropping the benzophenone-3 to 3% (FN5-849-14), reducing the SPF values markedly. FN5-849-23 again had high SPF values.

The 10% octocrylene would be expensive and had an odor so it was decided to try 8% octyl dimethyl PABA with 6% benozphenone-3, 10% IMP, and 4% Lexol PG (P.G. dioctanoate). See FN6-849-26 in Table I. Accordingly, FN6-849-34 was also prepared increasing the Lexol PG to 10%, providing good SPF values of from about 12 to 23.

When OD PABA was eliminated, the SPF values also fell (FN6-849-36) as was the case when the benzophenone-3 was again reduced to 3% (FN6-849-40). One reason for the problem was considered to be the solubility and distribution of benzophenone-3 in the oil-phase. Perhaps a combination of different oil-soluble components might help, so 5% isodecyl neopentanoate was substituted for 5% P.G. dioctanoate in FN6-849-48 and 7% octyl methoxycinnamate was added. The SPF values were less than 29.0, the highest values obtained to date, but the product still had OD PABA present. But in FN6-872-04, substitution of 10% octocrylene in place of 8% OD PABA with the other constituents remaining the same gave reduced SPF values again, so perhaps octocrylene really wasn't needed.

Finally, in W 1074-M-27-A, a correct combination of ingredients was found. We replaced the octocrylene with 7% octyl methoxycinnamate and 3% water, and used 6% benzophenone-3 and 5% octyl salicylate, and importantly, we solubilized the ingredients in a high oil phase system. The Ganex V-220 polymer solubilized and helped distribute the sunscreens and made them substantive. Also important is that the SPF values met the waterproof claim requirement of 80 minutes in a whirlpool or swimming pool. Thus Amphisol, Ganex V-216 or V-220, P.G. dioctanoate, isodecyl neopentanoate, and isopropyl myristate in the right proportions are necessary in order to solubilize and distribute all of the sunscreen agents properly so as to obtain a high SPF. The system appears to promote a uniform and effective distribution of the components, thereby providing even sun protection.

Furthermore, and also importantly, the high oil phase pharmaceutical vehicles and sunscreens of this invention have excellent skin-feel, i.e., they are very smooth and spreadable on the skin and possess good moisturizing properties. This is an important factor from the commerical aspect of consumer acceptance.

It should be noted that Table I lists only the major ingredients of each composition. Complete listings of ingredients and methods for making some of the sunscreens of this invention are as follows:

| FORMULA PRESUN 4 Creamy, W 1072-M-16-A | % |
|---|---|
| Octyl Dimethyl PABA | 2.0 |
| Water | 58.8 |
| Propylene Glycol Dioctanoate | 16.0 |
| Isopropyl Myristate | 10.0 |
| PVP/Eicosene Copolymer | 5.0 |
| Stearic Acid | 3.0 |
| Cetyl Phosphate and DEA Cetyl Phosphate | 2.5 |
| Dimethicone 225 | 1.0 |
| Cetyl Alcohol | 1.0 |
| Perfume R-6002 | 0.3 |
| Diazolidinyl Urea | 0.2 |
| Carbomer 940 | 0.1 |
| Triethanolamine | 0.1 |
| Methylchloroisothiazolinone and Methylisothiazolinone | 0.05 |
| | 100.0 |

MANUFACTURING DIRECTIONS

Product: PRESUN 4 Creamy Lotion, W 1072-M-16-A

1. Charge 99% of required water into a suitably sized main mix vessel fitted with a high speed propeller agitator. With rapid mixing, slowly add Carbomer 940, continue mixing until powder is completely in solution. Next, with moderate mixing, add Diazolidinyl Urea and Methylchloroisothiazolinone and Methylisothiazolinone. Start heating, and continue mixing until temperature reaches 70°–75° C. and mixture is homogeneous. This is water phase.
2. To a suitably sized premix vessel, add Propylene Glycol Dioctanoate, heat to 70°–75° C., then with moderate mixing add: Isopropyl Myristate, Dimethicone 225, Cetyl Alcohol, Stearic Acid, Octyl Dimethyl PABA, and PVP/Eicosene Copolymer. Mix until uniform, then add Cetyl Phosphate and DEA Cetyl Phosphate. Continue mixing until uniform. This is oil phase.

3. In a suitably sized premix vessel, add remaining water (the 1% saved from Step 1), then add Triethanolamine and mix until uniform solution is formed.
4. With Step 1 water phase at proper temperature (70°–75° C.), slowly add to water phase, the Step 3 solution, continue mixing until uniform.
5. Then, with Step 2 oil phase at the proper temperature (70°–75° C.), add the oil phase slowly, and with rapid mixing, to the Step 4 water phase. Continue mixing rapidly until emulsion is formed, then cool with continued mixing to 30° C. or less and add perfume. Mix until product is uniform.

ALTERNATE MANUFACTURING DIRECTIONS

Product: PRESUN 4, Creamy Lotion, W 1072-M-16-A

1. Charge 98.5% of the required water into a suitably sized premix vessel fitted with a high speed propeller agitator. Heat to 40°–45° C., then slowly add Carbomer 940 with rapid mixing. Continue mixing until powder is in solution. This is water phase.
2. To a suitably sized main mix vessel, add Propylene Glycol Dioctanoate. Heat to 70°–75° C., then add, with moderate mixing, Isopropyl Myristate, PVP/Eicosene Copolymer, Octyl Dimethyl PABA, Dimethicone, Cetyl Alcohol, Stearic Acid, and DEA Cetyl Phosphate. Mix until uniform. Maintain temperature at 70°–75° C., and moderate mixing.
3. With turbine mixing, add Step 1 water phase to the Step 2 oil phase. Mix until emulsion is formed and product is uniform. Begin cooling to 45° C. or lower.
4. To a suitably sized premix vessel, add 1% of the required water, start mixing and add Diazolidinyl Urea and Methylchloroisothiazolinone and Methylisothiazolinone. Mix until dissolved and uniform.
5. To a suitably sized small vessel, add ½% of the required water, then add Triethanolamine and mix until a clear solution is formed.
6. To Step 2 emulsion, add Step 4 solution. Mix and continue cooling to 30° C. or lower, then add Step 5 Triethanolamine solution. Continue mixing until product is uniform.

FORMULA
PRESUN 8 Creamy Lotion, W 1073-M-15-A

| | % |
|---|---|
| Octyl Dimethyl PABA | 4.0 |
| Benzophenone-3 | 3.0 |
| Water | 55.8 |
| Propylene Glycol Dioctanoate | 14.0 |
| Isopropyl Myristate | 10.0 |
| PVP/Eicosene Copolymer | 5.0 |
| Stearic Acid | 3.0 |
| Cetyl Phosphate and DEA Cetyl Phosphate | 2.5 |
| Dimethicone 225 | 1.0 |
| Cetyl Alcohol | 1.0 |
| Perfume R-6002 | 0.3 |
| Diazolidinyl Urea | 0.2 |
| Carbomer 940 | 0.1 |
| Triethanolamine | 0.1 |
| Methylchloroisothiazolinone and Methylisothiazolinone | 0.05 |
| | 100.0 |

MANUFACTURING DIRECTIONS

Product: PRESUN 8 Creamy Lotion, W 1073-M-15-A

1. Charge 99% of required water into a suitably sized main mix vessel fitted with a high speed propeller agitator. With rapid mixing, slowly add Carbomer 940, continue mixing until powder is completely in solution. Next, with moderate mixing, add Diazolidinyl Urea and Methylchloroisothiazolinone and Methylisothiazolinone. Start heating, and continue mixing until temperature reaches 70°–75° C. and mixture is homogeneous. This is water phase.
2. To a suitably sized premix vessel, add Propylene Glycol Dioctanoate, heat to 70°–75° C., then with moderate mixing add: Isopropyl Myristate, Dimethicone 225, Cetyl Alcohol, Stearic Acid, Benzophenone-3, Octyl Dimethyl PABA, and PVP/Eicosene Copolymer. Mix until uniform, then add Cetyl Phosphate and DEA Cetyl Phosphate. Continue mixing until uniform. This is oil phase.
3. In a suitably sized premix vessel, add remaining water (the 1% saved from Step 1), then add Triethanolamine and mix until uniform solution is formed.
4. With Step 1 water phase at proper temperature (70°–75° C.), slowly add to water phase, the Step 3 solution, continue mixing until uniform.
5. Then, with Step 2 oil phase at the proper temperature (70°–75° C.), add the oil phase slowly, and with rapid mixing, to the Step 4 water phase. Continue mixing rapidly until emulsion is formed, then cool with continued mixing to 30° C. or less and add perfume. Mix until product is uniform.

ALTERNATE MANUFACTURING DIRECTIONS

Product: PRESUN 8 Creamy Lotion, W 1073-M-15-A

1. Charge 98.5% of the required water into a suitably sized premix vessel fitted with a high speed propeller agitator. Heat to 40°–45° C., then slowly add Carbomer 940 with rapid mixing. Continue mixing until powder is in solution. This is water phase.
2. To a suitably sized main mix vessel, add Propylene Glycol Dioctanoate. Heat to 70°–75° C., then add, with moderate mixing, Isopropyl Myristate, PVP/Eicosene Copolymer, Octyl Dimethyl PABA, Dimethicone, Cetyl Alcohol, Stearic Acid, Benzophenone-3, and DEA Cetyl Phosphate. Mix until uniform. Maintain temperature at 70°–75° C., and moderate mixing.
3. With turbine mixing, add Step 1 water phase to the Step 2 oil phase. Mix until emulsion is formed and product is uniform. Begin cooling to 45° C. or lower.

4. To a suitably sized premix vessel, add 1% of the required water, start mixing and add Diazolidinyl Urea and Methylchloroisothiazolinone and Methylisothiazolinone. Mix until dissolved and uniform.
5. To a suitably sized small vessel, add ½% of the required water, then add Triethanolamine and mix until a clear solution is formed.
6. To Step 2 emulsion, add Step 4 solution. Mix and continue cooling to 30° C. or lower, then add Step 5 Triethanolamine solution. Continue mixing until product is uniform.

FORMULA
PRESUN 15 Creamy Lotion, W 1074-M-28-A

| | % |
|---|---|
| Benzophenone-3 | 6.0 |
| Octyl Dimethyl PABA | 5.0 |
| Water | 47.8 |
| Isopropyl Myristate | 10.0 |
| Propylene Glycol Dioctanoate | 10.0 |
| Isodecyl Neopentanoate | 8.0 |
| PVP/Eicosene Copolymer | 5.0 |
| Stearic Acid | 3.0 |
| Cetyl Phosphate and DEA Cetyl Phosphate | 2.5 |
| Cetyl Alcohol | 1.0 |
| Dimethicone 225 | 1.0 |
| Perfume R-6002 | 0.3 |
| Diazolidinyl Urea | 0.2 |
| Carbomer 940 | 0.1 |
| Triethanolamine | 0.1 |
| Methylchloroisothiazolinone and Methylisothiazolinone | 0.05 |
| | 100.0 |

MANUFACTURING DIRECTIONS

Product: PRESUN 15 Creamy Lotion, W 1074-M-28-A

1. Charge 99% of required water into a suitably sized main mix vessel fitted with a high speed propeller agitator. With rapid mixing, slowly add Carbomer 940, continue mixing until powder is completely in solution. Next, with moderate mixing, add Diazolidinyl Urea and Methylchloroisothiazolinone and Methylisothiazolinone. Start heating, and continue mixing until temperature reaches 70°-75° C. and mixture is homogeneous. This is water phase.
2. To a suitably sized premix vessel, add Propylene Glycol Dioctanoate, heat to 70°-75° C., then with moderate mixing add: Isopropyl Myristate, Dimethicone 225, Cetyl Alcohol, Stearic Acid, Benzophenone-3, Octyl Dimethyl PABA, and PVP/Eicosene Copolymer. Mix until uniform, then add Cetyl Phosphate and DEA Cetyl Phosphate. Continue mixing until uniform. This is oil phase.
3. In a suitably sized premix vessel, add remaining water (the 1% saved from Step 1), then add Triethanolamine and mix until uniform solution is formed.
4. With Step 1 water phase at proper temperatue (70°-75° C.), slowly add to water phase, the Step 3 solution, continue mixing until uniform.
5. Then, with Step 2 oil phase at the proper temperature (70°-75° C.), add the oil phase slowly, and with rapid mixing, to the Step 4 water phase. Continue mixing rapidly until emulsion is formed, then cool with continued mixing to 30° C. or less and add perfume. Mix until product is uniform.

ALTERNATE MANUFACTURING DIRECTIONS

Product: PRESUN 15 Creamy Lotion, W 1074-M-28-A

1. Charge 98.5% of the required water into a suitably sized premix vessel fitted with a high speed propeller agitator. Heat to 40°-45° C., then slowly add Carbomer 940 with rapid mixing. Continue mixing until powder is in solution. This is water phase.
2. To a suitably sized main mix vessel, add Propylene Glycol Dioctanoate. Heat to 70°-75° C., then add, with moderate mixing, Isopropyl Myristate, PVP/Eicosene Copolymer, Octyl Dimethyl PABA, Dimethicone, Cetyl Alcohol, Stearic Acid, Benzophenone-3, and DEA Cetyl Phosphate. Mix until uniform. Maintain temperature at 70°-75° C., and moderate mixing.
3. With turbine mixing, add Step 1 water phase to the Step 2 oil phase. Mix until emulsion is formed and product is uniform. Begin cooling to 45° C. or lower.
4. To a suitably sized premix vessel, add 1% of the required water, start mixing and add Diazolidinyl Urea and Methylchloroisothiazolinone and Methylisothiazolinone. Mix until dissolved and uniform.
5. To a suitably sized small vessel, add ½% of the required water, then add Triethanolamine and mix until a clear solution is formed.
6. To Step 2 emulsion, add Step 4 solution. Mix and continue cooling to 30° C. or lower, then add Step 5 Triethanolamine solution. Continue mixing until product is uniform.

FORMULA
PRESUN 29 Non-PABA Lotion

| | % |
|---|---|
| Octyl Methoxycinnamate | 7.0 |
| Benzophenone-3 | 6.0 |
| Octyl Salicylate | 5.0 |
| Water | 46.0 |
| Isopropyl Myristate | 10.0 |
| Propylene Glycol Dioctanoate | 8.0 |
| PVP/Eicosene Copolymer | 5.0 |
| Isodecyl Neopentanoate | 5.0 |
| Stearic Acid | 3.0 |
| Cetyl Phosphate and DEA Cetyl Phosphate | 2.5 |
| Cetyl Alcohol | 1.0 |
| Dimethicone 225 | 1.0 |
| Diazolidinyl Urea | 0.2 |
| Carbomer 490 | 0.1 |
| Triethanolamine | 0.1 |
| Methylchloroisothiazolinone and Methylisothiazolinone | 0.05 |
| | 100.0 |

MANUFACTURING DIRECTIONS

Product: PRESUN 29 Non-PABA Lotion, W 1074-M-27-A

1. Charge 99% of required water into a suitably sized main mix vessel fitted with a high speed propeller agitator. With rapid mixing, slowly add Carbomer 940, continue mixing until powder is completely in solution. Next, with moderate mixing, add Diazolidinyl Urea and Methylchloroisothiazolinone and Methylisothiazolinone. Start heating, and continue mixing until temperature reaches 70°-75° C. and mixture is homogeneous. This is water phase.
2. To a suitably sized premix vessel, add Propylene Glycol Dioctanoate, heat to 70°-75° C., then with moderate mixing add: Isopropyl Myristate, Dimethicone 225, Cetyl Alcohol, Stearic Acid, Benzophenone-3, Octyl Salicylate, Octyl Methoxycinnamate, PVP/Eicosene Copolymer and Isodecyl Neopentanoate. Mix until uniform, then add Cetyl Phosphate and DEA Cetyl Phosphate. Continue mixing until uniform. This is oil phase.

3. In a suitably sized premix vessel, add remaining water (the 1% saved from Step 1), then add Triethanolamine and mix until uniform solution is formed.

4. With Step 1 water phase at proper temperature (70°–75° C.), slowly add to water phase, the Step 3 solution, continue mixing until uniform.

5. Then, with Step 2 oil phase at the proper temperature (70°–75° C.), add the oil phase slowly, and with rapid mixing, to the Step 4 water phase. Continue mixing rapidly until emulsion is formed, then cool with continued mixing to 30° C. or less and add perfume. Mix until product is uniform.

ALTERNATE MANUFACTURING DIRECTIONS

Product: PRESUN 29 Non-PABA Lotion, W 1074-M-27-A

1. Charge 98.5% of the required water into a suitably sized premix vessel fitted with a high speed propeller agitator. Heat to 40°–45° C., then slowly add Carbomer 940 with rapid mixing. Continue mixing until powder is in solution. This is water phase.

2. To a suitably sized main mix vessel, add PVP/Eicosene Copolymer, Propylene Glycol Dioctanoate and Octyl Methoxycinnamate, heat to 70°–75° C., then add, with moderate mixing, Isopropyl Myristate, Isodecyl Neopentanoate, Octyl Salicylate, Dimethicone, Cetyl Alcohol, Stearic Acid, Benzophenone-3, and DEA Cetyl Phosphate. Mix until uniform. Maintain temperature at 70°–75° C., and moderate mixing.

3. With turbine mixing, add Step 1 water phase to the Step 2 oil phase. Mix until emulsion is formed and product is uniform. Begin cooling to 45° C. or lower.

4. To a suitably sized premix vessel, add 1% of the required water, start mixing and add Diazolidinyl Urea and Methylchloroisothiazolinone and Methylisothiazolinone. Mix until dissolved and uniform.

5. To a suitably sized small vessel, add ½% of the required water, then add Triethanolamine and mix until a clear solution is formed.

6. To Step 2 emulsion, add Step 4 solution. Mix and continue cooling to 30° C. or lower, then add Step 5 Triethanolamine solution. Continue mixing until product is uniform.

The present invention has been described with respect to several the preferred embodiments. It will be clear to those skilled in the art that modifications and or variations of the disclosed compositions may be made without departing from the scope of the invention as set forth in the appended claim.

We claim:

1. A waterproof pharmaceutical vehicle in the form of an aqueous emulsion system having an oil phase content of from about 35% to about 65%, wherein the emulsion system comprises:
    from about 1% to about 10% of an oil soluble polyvinylpyrrolidone and long alkyl chain olefin copolymer;
    from about 2% to about 10% of an emulsifier; and
    a solvent system comprising
        from about 4% to about 20% of a $C_4$–$C_{22}$ fatty acid, alcohol or ester thereof,
        from about 4% to about 25% of a glycol ester or glycol diester, and
        from 0% to about 13% of a branched chain ester of a $C_4$–$C_{22}$ carboxylic acid.

2. The pharmaceutical vehicle of claim 1 wherein the copolymer comprises a copolymer of polyvinylpyrrolidone and hexadecene or a copolymer of polyvinylpyrrolidone and licosene.

3. The pharmaceutical vehicle of claim 2 wherein the copolymer is present in an amount of from about 2.5% to about 7.5%.

4. The pharmaceutical vehicle of claim 3 wherein the emulsifier comprises cetyl phosphate and DEA cetyl phosphate.

5. The pharmaceutical vehicle of claim 4 wherein the emulsifier is present in an amount of from about 2% to 5%.

6. The pharmaceutical vehicle of claim 2 wherein the solvent system comprises from about 6% to about 15% of isopropyl myristate and from about 4% to about 20% of propylene glycol dioctanoate.

7. The pharmaceutical vehicle of claim 6 comprising additionally from about 3% to about 13% of isodecyl neopentanoate.

8. The pharmaceutical vehicle of claim 6 wherein the copolymer comprises a copolymer of polyvinylpyrrolidone and licosene.

9. The pharmaceutical vehicle of claim 7 wherein the copolymer comprises a copolymer of polyvinylpyrrolidone and licosene.

* * * * *